(12) United States Patent
Sazanami et al.

(10) Patent No.: US 8,252,272 B2
(45) Date of Patent: Aug. 28, 2012

(54) HAIR COSMETIC COMPOSITION

(75) Inventors: Fumiko Sazanami, Sumida-ku (JP);
Hiroto Tanamachi, Sumida-ku (JP);
Mio Ishita, Haga-gun (JP)

(73) Assignee: Kao Corporation, Tokyo (JP)

( * ) Notice: Subject to any disclaimer, the term of this patent is extended or adjusted under 35 U.S.C. 154(b) by 282 days.

(21) Appl. No.: 12/130,486

(22) Filed: May 30, 2008

(65) Prior Publication Data

US 2008/0299063 A1    Dec. 4, 2008

(30) Foreign Application Priority Data

May 31, 2007   (JP) .................................. 2007-146270
May 31, 2007   (JP) .................................. 2007-146271

(51) Int. Cl.
*A61K 8/00* (2006.01)
*A61Q 5/12* (2006.01)

(52) U.S. Cl. .................................. 424/70.12; 424/70.1
(58) Field of Classification Search .................. None
See application file for complete search history.

(56) References Cited

U.S. PATENT DOCUMENTS

| | | | | |
|---|---|---|---|---|
| 5,476,649 | A | * | 12/1995 | Naito et al. .................. 424/70.1 |
| 6,685,953 | B1 | * | 2/2004 | Hoshino et al. ............... 424/401 |
| 2003/0147822 | A1 | * | 8/2003 | Doi et al. ...................... 424/70.1 |
| 2004/0115162 | A1 | | 6/2004 | Hoshino et al. |
| 2009/0068134 | A1 | | 3/2009 | Kaharu |

FOREIGN PATENT DOCUMENTS

| | | |
|---|---|---|
| CN | 1347312 | 5/2002 |
| JP | 4-164014 | 6/1992 |
| JP | 4-173719 | 6/1992 |
| JP | 9-71516 | 3/1997 |
| JP | 9-71517 | 3/1997 |
| JP | 10-236927 | 9/1998 |
| JP | 2001-163733 | 6/2001 |
| JP | 2001-172129 | 6/2001 |
| JP | 2001-508060 | 6/2001 |
| JP | 2003-81779 | 3/2003 |
| JP | 2003-81780 | 3/2003 |
| JP | 2003-81781 | 3/2003 |
| JP | 2003-171238 | 6/2003 |
| JP | 2003-300835 | 10/2003 |
| JP | 2004-67534 | 3/2004 |
| JP | 2004-323491 | 11/2004 |
| JP | 2005-29564 | 2/2005 |
| JP | 2005-68047 | 3/2005 |
| JP | 2005-179197 | 7/2005 |
| JP | 2005-187403 | 7/2005 |
| JP | 2005-232113 | 9/2005 |
| JP | 2005-298447 | 10/2005 |
| JP | 2006-8610 | 1/2006 |
| JP | 2006-182702 | 7/2006 |
| JP | 2006-225307 | 8/2006 |
| JP | 2008-127337 | 6/2008 |
| WO | WO 2006/109877 | 10/2006 |

OTHER PUBLICATIONS

Vincent Dupres, et al., "Wetting and electrical properties of the human hair surface: Delipidation observed at the nanoscale", Journal of Colloid and Interface Science, vol. 306, No. 1, Oct. 21, 2006, pp. 31-40.

Chinese Office Action issued on May 5, 2011, in China Patent Application No. 200810098414.7, filed May 26, 2008.

* cited by examiner

*Primary Examiner* — Brian Gulledge
(74) *Attorney, Agent, or Firm* — Oblon, Spivak, McClelland, Maier & Neustadt, L.L.P.

(57) ABSTRACT

Provided is a hair cosmetic composition containing (A) an amidoamine (1) or an etheramine (2), or a salt thereof, (B) a branched fatty acid (3) or a salt thereof, (C) a silicone, and water:

$$R^1-CONH-(CH_2)_m-N(R^2)_2 \quad (1)$$

$$R^3-O-(CH_2)_3-\underset{R^5}{\overset{R^4}{\underset{|}{\overset{|}{N}}}} \quad (2)$$

$$CH_3-\underset{R^6}{\overset{H}{\underset{|}{\overset{|}{C}}}}-(CH_2)_p-COOH \quad (3)$$

in the formula (1), $R^1$ represents an aliphatic $C_{11-23}$ hydrocarbon group, $R^2$ represents H or a $C_{1-4}$ alkyl group, and m stands for a number from 2 to 4; in the formula (2), $R^3$ represents a $C_{6-24}$ alkyl or alkenyl group, and $R^4$ and $R^5$ each represents a $C_{1-6}$ alkyl group or a group $-(AO)_nH$, in which A represents a $C_{2-4}$ alkylene group and n stands for a number from 1 to 6; and in the formula (3), $R^6$ represents a methyl or ethyl group, and p stands for a number from 3 to 36.

5 Claims, No Drawings

HAIR COSMETIC COMPOSITION

FIELD OF THE INVENTION

The present invention relates to a hair cosmetic composition containing a specific amine compound or a salt thereof.

BACKGROUND OF THE INVENTION

Hair tends to be excessively dry because it is always exposed to sunlight and cannot avoid the influence of ultraviolet rays, heat and drying. Daily shampooing, brushing and blow-drying also have an adverse influence. It has been elucidated that hair damage such as loss of luster or hair dryness due to blow-drying after shampooing occurs because a hollow comes out inside the hair by the heat from a drier. In recent years, it has been common to enjoy changing the appearance of hair freely such as changing hair color (coloring) and changing hair style (permanent waving) so that coloring and permanent waving have been carried out with increased frequency. The hair subjected to coloring treatment or permanent waving treatment is said to become hollow due to chemical influence of a hair dye or permanent waving agent used for the treatment. In addition, daily hair care routine (shampooing, finger combing, and brushing) continues to impose a small strain to the hair, whereby cracks, voids, cleavages, cuts or the like grow inside the hair.

Various attempts have therefore been made to repair hair damage. For the purpose of repairing or preventing hair damage and providing hair with an excellent feel, there are proposed, for example, a hair cosmetic composition using a specific amine compound or salt thereof, a higher alcohol, and an organic solvent in combination (JP-A-2003-81780 and JP-A-2004-67534) and a hair cosmetic composition containing a branched fatty acid (JP-A-4-173719 corresponding to EP-0483689 and U.S. Pat. No. 5,476,649).

However, these hair cosmetic compositions cannot satisfactorily provide a good feel to the heavily damaged hair caused by repetition of coloring or other treatments. Also they cannot satisfactorily repair or prevent fatigue failure of hair such as split ends or breakage. In addition, they cannot reduce crunch of hair during shampooing.

SUMMARY OF THE INVENTION

In the present invention, there is provided a hair cosmetic composition containing the following Components (A), (B) and (C) and water:

(A): an amidoamine represented by the following formula (1):

$$R^1\text{—CONH—}(CH_2)_m\text{—N}(R^2)_2 \quad (1)$$

(wherein, $R^1$ represents an aliphatic $C_{11-23}$ hydrocarbon group, $R^2$s may be the same or different and each represents a hydrogen atom or a $C_{1-4}$ alkyl group, and m stands for a number of from 2 to 4) or an etheramine represented by the following formula (2):

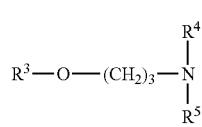

(wherein, $R^3$ represents a linear or branched $C_{6-24}$ alkyl or alkenyl group, $R^4$ and $R^5$ may be the same or different and each represents a $C_{1-6}$ alkyl group or a group —$(AO)_nH$, in which A represents a $C_{2-4}$ alkylene group, n stands for a number from 1 to 6, and n pieces of AOs may be the same or different and are arranged in any order), or a salt of the amidoamine or etheramine;

(B) a branched fatty acid represented by the following formula (3):

(wherein, $R^6$ represents a methyl or an ethyl group and p stands for an integer from 3 to 36), or a salt of the branched fatty acid; and (C) a silicone.

DETAILED DESCRIPTION OF THE INVENTION

The present invention relates to a hair cosmetic composition capable of repairing or preventing damage and/or fatigue failure of the hair due to chemical treatment, blow-drying or daily hair care routine and capable of providing the hair with good softness and suppleness during wetting and even after drying.

The present inventors have found that a hair cosmetic composition capable of satisfying the above-described demands is available using an amine compound selected from amidoamines and etheramines and salts thereof, a branched fatty acid, and a silicone in combination.

In the amidoamine to be used as Component (A) in the present invention, examples of the fatty acid residue (acyl group) represented by $R^1CO$ in the formula (1) include a lauroyl group, myristoyl group, palmitoyl group, stearoyl group, oleoyl group and behenoyl group. With regard to the composition of the fatty acid residues represented by $R^1CO$, it is preferred that fatty acid residues having 20 or greater carbon atoms amount to 60 wt. % or greater, fatty acid residues having 20 carbon atoms amount to 3 wt. % or greater, and fatty acid residues having 22 carbon atoms amount to from 50 to 95 wt. % in all the fatty acid residues, from the viewpoint of providing hair with good softness and improving its smoothness during wetting and even after drying. In view of smoothness after drying, the fatty acid residues having 20 or greater carbon atoms amount to preferably 75 wt. % or greater, more preferably 90 wt. % or greater; the fatty acid residues having 20 carbon atoms amount to preferably 4 wt. % or greater, more preferably 5 wt. % or greater; and the fatty acid residues having 22 carbon atoms amount to preferably from 55 to 95 wt. %, more preferably from 70 to 95 wt. %, even more preferably from 80 to 95 wt. %. As $R^2$, methyl, ethyl, and propyl groups are preferred, of which methyl group is especially preferred. As m, 2 or 3 is preferred.

Specific examples of the amidoamine include stearic acid dimethylaminoethylamide, stearic acid dimethylaminopropylamide, stearic acid diethylaminoethylamide, stearic acid diethylaminopropylamide, stearic acid dipropylaminoethylamide, stearic acid dipropylaminopropylamide, palmitic acid dimethylaminoethylamide, palmitic acid dimethylaminopropylamide, myristic acid dimethylaminoethylamide, myristic acid dimethylaminopropylamide, behenic acid dimethylaminoethylamide, behenic acid dimethylaminopropylamide, arachidic acid dimethylaminoethylamide, and arachidic acid dimethylaminopropylamide. Of these, stearic acid diethylaminoethylamide and stearic acid dimethylaminopropylamide are preferred from the standpoints of performance, stability and easy availability.

In the etheramine to be used as Component (A) in the present invention, $R^3$ in the formula (2) is a linear or branched $C_{6-24}$ alkyl or alkenyl group. From the viewpoint of providing good softness and smoothness to the hair during wetting and even after drying and particularly excellence in smoothness after drying, it is preferably a linear or branched $C_{12-24}$, more preferably $C_{14-22}$ alkyl or alkenyl group, of which the alkyl group is even more preferred.

$R^4$ and $R^5$ each independently represents a $C_{1-6}$ alkyl group or a group $—(AO)_nH$ (A and n having the same meanings as described above). From the viewpoint of providing good softness and smoothness to the hair during wetting and even after drying and particularly excellence in smoothness after drying, it is preferably a $C_{1-6}$ alkyl group or $—(CH_2CH_2O)_nH$ (n standing for from 1 to 3, preferably 1). More preferably, at least one of $R^4$ and $R^5$ represents a $C_{1-6}$ alkyl group, more preferably a methyl or an ethyl group. Even more preferably, they represent the same group.

Specific preferred examples of the etheramine include N,N-dimethyl-3-hexadecyloxypropylamine and N,N-dimethyl-3-octadecyloxypropylamine.

It is preferred that all or a part of the amidoamines and etheramines to be used in the present invention are neutralized with an inorganic or organic acid.

Examples of the inorganic acid include hydrochloric acid, sulfuric acid and phosphoric acid. Examples of the organic acid include monocarboxylic acids such as acetic acid and propionic acid; dicarboxylic acids such as malonic acid, succinic acid, glutaric acid, adipic acid, maleic acid, fumaric acid, and phthalic acid; polycarboxylic acids such as polyglutamic acid; hydroxycarboxylic acids such as glycolic acid, lactic acid, hydroxyacrylic acid, glyceric acid, malic acid, tartaric acid, and citric acid; and acidic amino acids such as glutamic acid and aspartic acid. of these, the inorganic acids, dicarboxylic acids, hydroxycarboxylic acids, and acidic amino acids are preferred. As the inorganic acid, hydrochloric acid is preferred. As the dicarboxylic acid, maleic acid and succinic acid are preferred. As the hydroxycarboxylic acid, glycolic acid, lactic acid, and malic acid are preferred. As the acidic amino acid, glutamic acid is preferred.

As the organic acid, the branched fatty acid as Component (B) may be employed. The amidoamine and/or etheramine may be mixed and neutralized with the branched fatty acid in advance to be used as an acid addition salt. In the hair cosmetic composition of the present invention, Component (A) and Component (B) are presumed to form a hydrophobic composite.

The inorganic acid and/or organic acid are added preferably in an amount of from 0.1 to 10 moles, more preferably from 0.3 to 4 moles per mole of the amidoamine and/or etheramine as Component (A) in order to effectively reduce an amine odor and to improve conditioning effects like the softness and smoothness of the hair.

As Component (A), two or more of the amidoamines and etheramines, and salts thereof may be used in combination. The content thereof, in terms of all the amine even in the case of a salt, is preferably from 0.1 to 20 wt. %, more preferably from 0.3 to 15 wt. %, even more preferably from 0.5 to 10 wt. % in order to provide good softness and smoothness to the hair upon use of the composition.

The branched fatty acid as Component (B) can be isolated or extracted from the hair or the like in accordance with, for example, the description in *LIPIDS*, 23(9), 878-881(1988) or WO98/30532. It can also be synthesized in accordance with the description of JP-A 4-173719. The branched fatty acid is represented by the formula (3) and has preferably from 7 to 40 carbon atoms, more preferably from 8 to 30 carbon atoms, even more preferably from 10 to 22 carbon atoms, each in total. Specific examples include 18-methyleicosanoic acid, 14-methylpentadecanoic acid, 14-methylhexadecanoic acid, 15-methylhexadecanoic acid, 15-methylheptadecanoic acid, 16-methylheptadecanoic acid, 16-methyloctadecanoic acid, 17-methyloctadecanoic acid, and 17-methylnonadecanoic acid. Examples of the salts of these branched fatty acids include alkali metal salts such as sodium salts, lithium salts, and potassium salts; alkaline earth metal salts such as calcium salts and magnesium salts; ammonium salts; organic amine salts such as triethanolamine salts, diethanolamine salts, and monoethanolamine salts; and basic amino acid salts such as lysine salts and arginine salts.

Examples of the branched fatty acid obtained by extraction include lanolin fatty acid and salts thereof obtained by extraction of lanolin. The lanolin fatty acid contains approximately 50 wt. % of a methyl-branched long-chain fatty acid which is called iso fatty acid or anteiso fatty acid. Specific examples include "Crodacid 18-MEA" (trade name; product of Croda Japan), "Skliro" (trade name; product of Croda Japan), and "FA-NH" (trade name; product of Nippon Fine Chemical).

As Component (B), two or more of the branched fatty acids and salts thereof may be used in combination. The synthesized branched fatty acid and extracted one may be used as a mixture. The content thereof is preferably from 0.01 to 10 wt. %, more preferably from 0.05 to 5 wt. % in the hair cosmetic composition of the present invention in view of an effect for repairing or preventing hair damage.

In addition, a water content in the hair cosmetic composition of the present invention is from 50 to 95 wt. %, more preferably from 60 to 90 wt. %.

The following are examples of silicones to be used as Component (C).

(i) Highly polymerized dimethylpolysiloxanes

Examples include "BY11-026" and "BY22-19" (each, trade name; product of Dow Corning Toray), and "FZ-3125" (trade name; product of Nippon Unicar).

The highly polymerized dimethylpolysiloxane dissolved or dispersed in a liquid oil (for example, liquid silicone oil such as the following (ii) dimethylpolysiloxane oil and (iii) cyclic silicone oil, or liquid hydrocarbon oil such as isoparaffin) can also be used.

(ii) Dimethylpolysiloxane oil represented by the following formula:

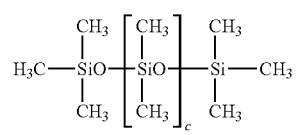

(wherein, c stands for an integer from 0 to 650).

Specific examples include commercially available products such as "SH200C Series, 1 CS, 50 CS, 200 CS, 1000 CS and 5000 CS" (each product of Dow Corning Toray).

(iii) Cyclic silicones represented by the following formula:

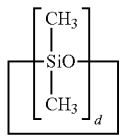

(wherein, d stands for an integer from 3 to 7).

Specific examples include dodecamethylcyclohexasiloxane, octamethylcyclotetrasiloxane and decamethylcyclopentasiloxane. Examples of the commercially available product include "SH244" and "SH245" (each, trade name; product of Dow Corning Toray).

(iv) Amino-modified silicones represented by the following formula:

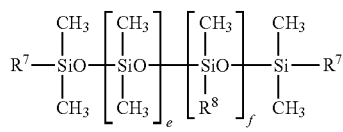

(wherein, $R^7$ represents a methyl or hydroxy group or the same group as $R^8$, $R^8$ represents a reactive functional group represented by —$R^9$-Q (in which $R^9$ represents a divalent $C_{3-6}$ hydrocarbon group and Q represents a group containing a primary, secondary or tertiary amino group or an ammonium group), and e and f each stands for a positive integer and e+f varies depending on the molecular weight). Preferable average molecular weight is from 3000 to 100000.

Examples include "SS-3551", "SF8452C", "DC929", and "DC8500" (each, trade name; product of Down Corning Toray) and "KT 1989" (trade name; product of Momentive Performance Materials). When the amino-modified silicone is used in the form of an aqueous emulsion, the amount of the amino-modified silicone contained in the aqueous emulsion is preferably from 20 to 60 wt. %, more preferably from 30 to 50 wt. %. Preferred examples of the aqueous emulsion of an amino-modified silicone include "SM8704C" (trade name; product of Dow Corning Toray).

(v) Other silicones

Examples of the silicone other than those described above include polyether modified silicones, methylphenylpolysiloxane, fatty acid modified silicones, alcohol modified silicones, alkoxy modified silicones, epoxy modified silicones, fluorine modified silicones, and alkyl modified silicones.

The content of the silicone compound is preferably from 0.1 to 15 wt. %, more preferably from 0.5 to 10 wt. % in the hair cosmetic composition.

The hair cosmetic composition of the present invention may further contain an amphipathic amide lipid as Component (D) in order to improve the external repairing effect of the hair. Examples of the amphipathic amide lipid include those selected from diamide compounds represented by the formula (4) and ceramides (and homologs thereof) represented by the formula (5).

(i) Diamide compounds represented by the formula (4):

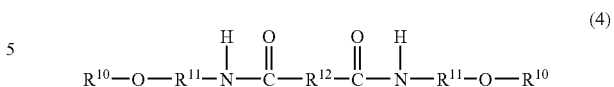

(wherein, $R^{10}$ represents a linear or branched $C_{1-12}$ hydrocarbon group which may be substituted with a hydroxy group and/or alkoxy group, $R^{11}$ represents a linear or branched divalent $C_{1-5}$ hydrocarbon group, and $R^{12}$ represents a linear or branched divalent $C_{1-22}$ hydrocarbon group).

As $R^{10}$ in the formula (4), linear or branched $C_{1-12}$ alkyl groups which may be substituted with from 1 to 3 groups selected from a hydroxy group and $C_{1-6}$ alkoxy groups are preferred. Of these, unsubstituted $C_{1-12}$ alkyl groups and $C_{2-12}$ alkyl groups substituted with 1 or 2 hydroxy groups or with one $C_{1-6}$ alkoxy group or with one hydroxy group and one $C_{1-6}$ alkoxy group are more preferred. Specific examples include methyl, ethyl, propyl, butyl, hexyl, dodecyl, 2-methylpropyl, 2-ethylhexyl, 2-hydroxyethyl, 9-hydroxynonyl, 2,3-dihydroxypropyl, 2-methoxyethyl, 2-hydroxy-3-methoxypropyl and 9-methoxynonyl groups, of which 2-hydroxyethyl, methyl, dodecyl and 2-methoxyethyl groups are preferred.

As $R^{11}$ in formula (4), linear or branched $C_{2-5}$ alkylene groups are preferred, with linear or branched $C_{2-3}$ alkylene groups being more preferred. Specific examples include ethylene, trimethylene, tetramethylene, pentamethylene, 1-methylethylene, 2-methylethylene, 1-methyltrimethylene, 2-methyltrimethylene, 1,1-dimethylethylene and 2-ethyltrimethylene groups. Of these, ethylene and trimethylene groups are preferred.

As $R^{12}$ in formula (4), linear or branched divalent $C_{2-22}$ hydrocarbon groups are preferred, with linear or branched $C_{11-22}$ alkylene groups and alkenylene groups having from 1 to 4 double bonds being more preferred. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, ethenylene, 1-octadecenylethylene, 7,11-octadecadienylene, 7-ethenyl-9-hexadecamethylene, 7,12-dimethyl-7,11-octadecadienylene and 8,11-dimethyl-7,11-octadecadienylene groups. Of these, 7,12-dimethyloctadecamethylene, 7,12-dimethyl-7,11-octadecadienylene, octadecamethylene, undecamethylene, and tridecamethylene groups are preferred.

Preferred diamide compounds (4) are compounds having the above-described preferred groups as $R^{10}$, $R^{11}$ and $R^{12}$, respectively, in combination. Specific examples are the following compounds:

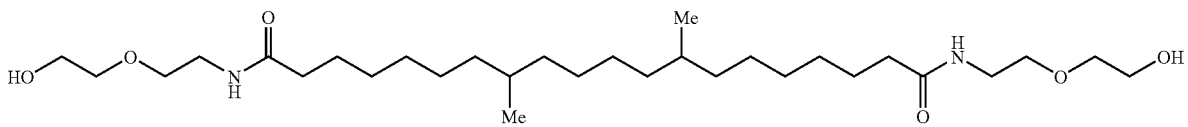

-continued
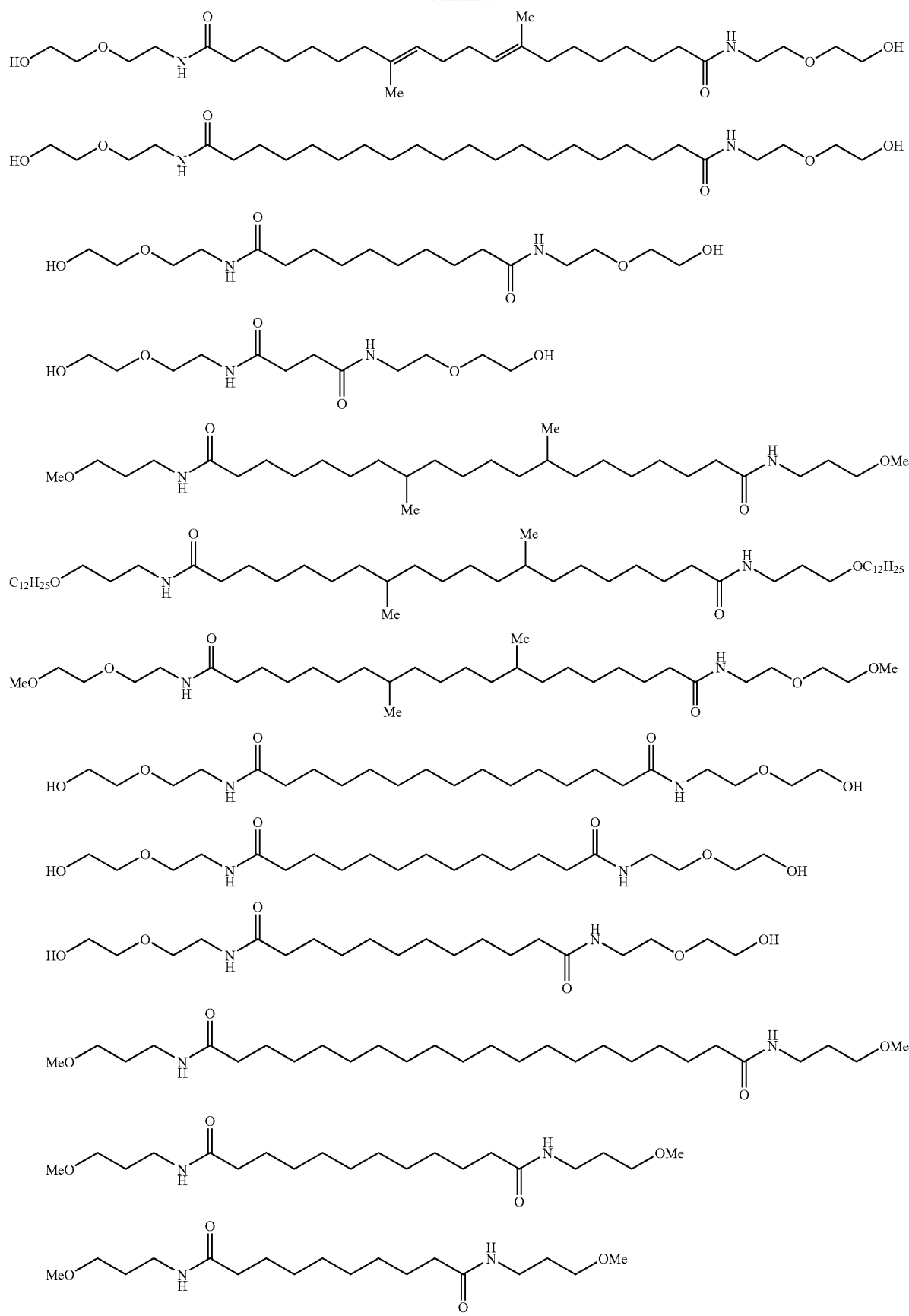

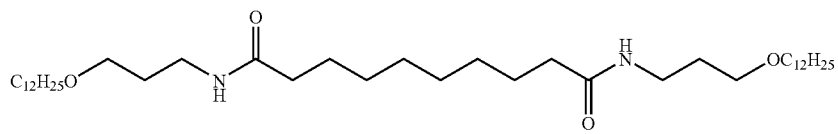

(ii) Ceramides and homologs thereof represented by the following formula (5):

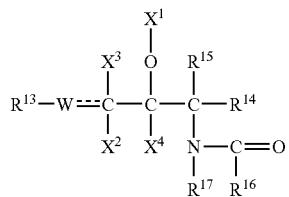

(wherein, $R^{13}$ represents a linear, branched or cyclic, saturated or unsaturated $C_{4-30}$ hydrocarbon group which may be substituted with a hydroxy, oxo, or amino group; W represents a methylene group, a methine group or an oxygen atom, a broken line represents the presence or absence of a π bond; $X^1$ represents a hydrogen atom, an acetyl group or a glyceryl group, or forms an oxo group together with the adjacent oxygen atom; $X^2$, $X^3$ and $X^4$ each independently represent a hydrogen atom, a hydroxy group or an acetoxy group, with the proviso that when W represents a methine group, either $X^2$ or $X^3$ represents a hydrogen atom and the other does not exist, and when —O—$X^1$ represents an oxo group, $X^4$ does not exist; $R^{14}$ and $R^{15}$ each independently represents a hydrogen atom, a hydroxy group, a hydroxymethyl group, or an acetoxymethyl group; $R^{16}$ represents a linear, branched or cyclic $C_{5-35}$ hydrocarbon group which may be substituted with a hydroxy or amino group, and which may have, at the ω-position, an ester-bonded or an amide-bonded $C_{8-22}$ fatty acid moiety that may be linear, branched or cyclic, and saturated or unsaturated, and may be substituted with a hydroxy group; and $R^{17}$ represents a hydrogen atom or a linear or branched, saturated or unsaturated $C_{1-8}$ hydrocarbon group which may be substituted with a hydroxy group, hydroxyalkoxy groups, alkoxy groups and an acetoxy group).

As $R^{13}$ in the formula (5), linear, branched or cyclic, saturated or unsaturated $C_{7-22}$ hydrocarbon groups which may be substituted with a hydroxy group are preferred. As $X^1$, a hydrogen atom and a glyceryl group are preferred. It is preferred that at most one of $X^2$, $X^3$, and $X^4$ represents a hydroxy group and the others represent a hydrogen atom. It is preferred that one of $R^{14}$ and $R^{15}$ represents a hydrogen atom or a hydroxymethyl group and the other represents a hydrogen atom. In $R^{16}$, preferred examples of the fatty acid which may be ester-bonded or amide-bonded to the ω-position of the hydrocarbon group include isostearic acid, 12-hydroxystearic acid and linoleic acid. As $R^{17}$, a hydrogen atom and $C_{1-8}$ hydrocarbon groups which may be substituted with 1 to 3 substituents selected from a hydroxy group, hydroxyalkoxy groups and alkoxy groups are preferred.

As the ceramide (5), preferred are natural ceramides and natural type ceramides, and derivatives thereof each represented by the following formula (5a) (which will hereinafter be called "natural type ceramides (5a)" and pseudo type ceramides represented by the formula (5b) (which will hereinafter be called "pseudo type ceramides (5b)).

(ii-1) Natural type ceramides (5a):

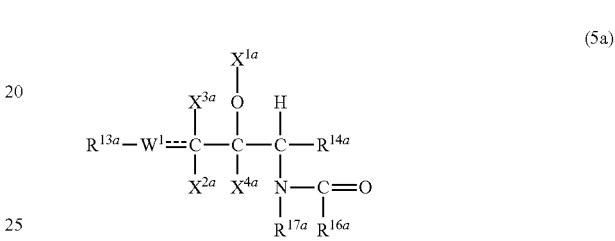

(wherein, $R^{13a}$ represents a linear, branched or cyclic, saturated or unsaturated $C_{7-19}$ hydrocarbon group which may be substituted with a hydroxy group; $W^1$ represents a methylene or methine group, a broken line represents the presence or absence of a π bond; $X^{1a}$ represents a hydrogen atom or forms an oxo group together with the adjacent oxygen atom; $X^{2a}$, $X^{3a}$ and $X^{4a}$ each independently represents a hydrogen atom, a hydroxy group, or an acetoxy group, with the proviso that when $W^1$ represents a methine group, one of $X^{2a}$ and $X^{3a}$ represents a hydrogen atom and the other does not exist, and when -O—$X^{1a}$ represents an oxo group, $X^{4a}$ does not exist; $R^{14a}$ represents a hydroxymethyl group or an acetoxymethyl group; $R^{16a}$ represents a linear, branched or cyclic $C_{5-30}$ alkyl group which may be substituted with a hydroxy group, and which may have, at the ω-end position, an ester-bonded $C_{8-22}$ fatty acid moiety that may be linear or branched, saturated or unsaturated, and may be substituted with a hydroxy group, and $R^{17a}$ represents a hydrogen atom or a $C_{1-4}$ alkyl group).

Preferred are compounds in which $R^{13a}$ is a linear $C_{7-19}$, more preferably $C_{13-15}$ alkyl group; $W^1$ is a methine group and one of $X^{2a}$ and $X^{3a}$ is a hydrogen atom; and $R^{16a}$ is a linear $C_{9-27}$ alkyl group which may be substituted with a hydroxy group. In addition, $X^{1a}$ preferably represents a hydrogen atom, or forms an oxo group together with an oxygen atom. Preferred examples of $R^{16a}$ include tricosyl group, 1-hydroxypentadecyl group, 1-hydroxytricosyl group, heptadecyl group, 1-hydroxyundecyl group, and nonacosyl group having a linoleic acid ester-bonded to the ω-position thereof.

Specific examples of the natural type ceramides include Ceramide Types 1 to 7 (for example, FIG. 2 of J. Lipid Res., 24, 759(1983), and pig and human ceramides described in FIG. 4. of J. Lipid Res., 35, 2069(1994)) having the structures as shown below and available by amidation of sphingosine, dihydrosphingosine, phytosphingosine, or sphingadienine. Furthermore, N-alkyl derivatives (for example, N-methyl derivatives) of these ceramides are also exemplified. They may be either an extract from natural sources or synthesized product. Commercially available ones can also be used.

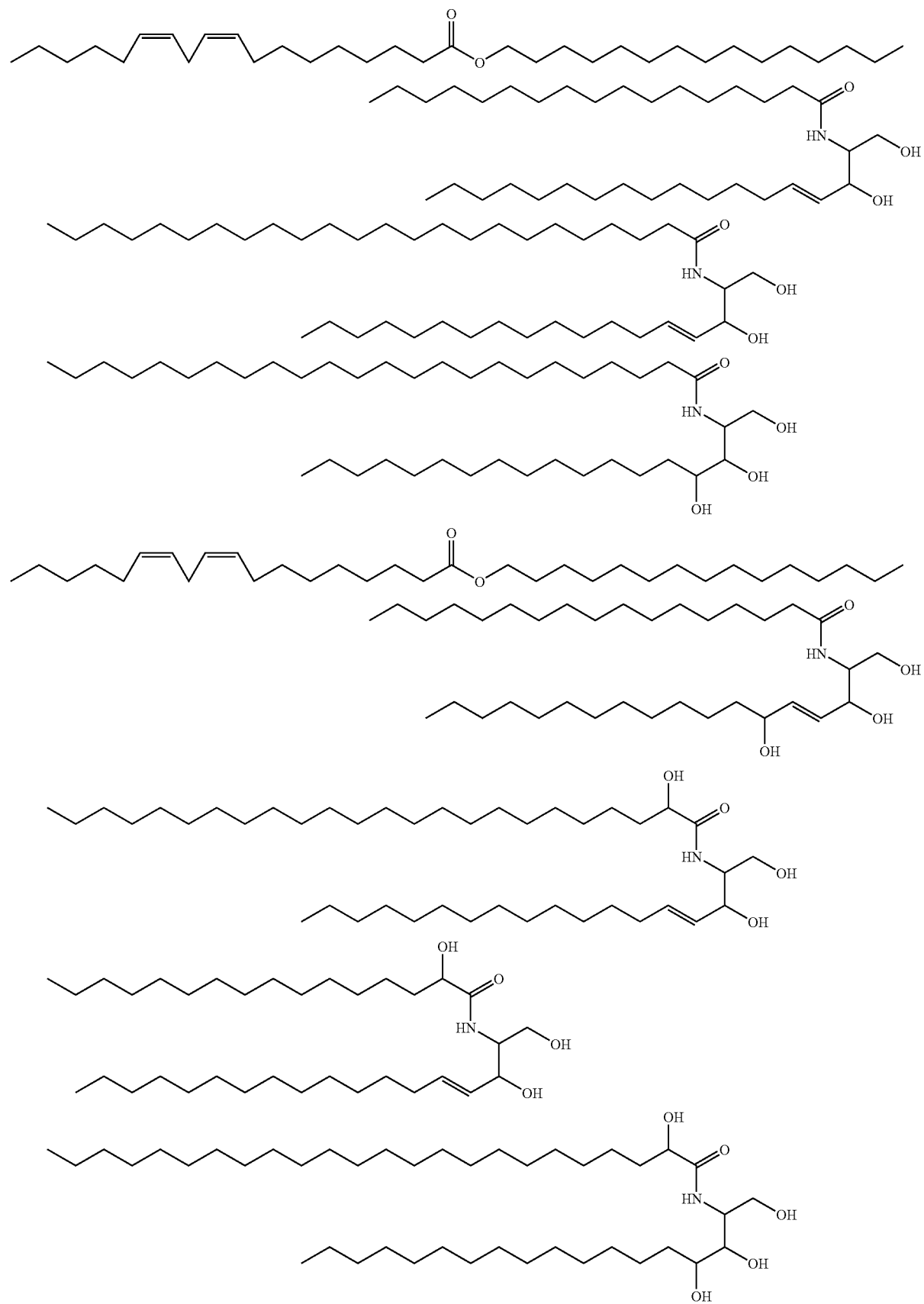

-continued

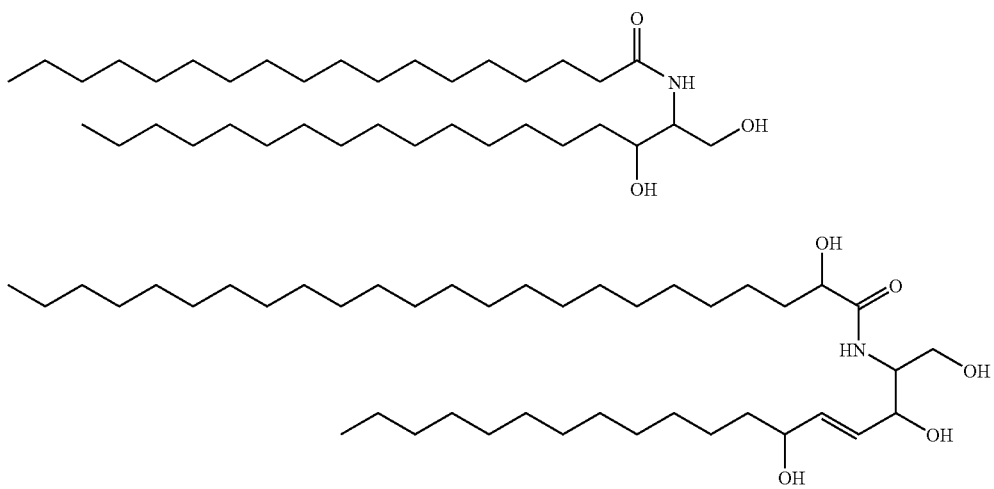

(ii-2) Pseudo type ceramides (5b):

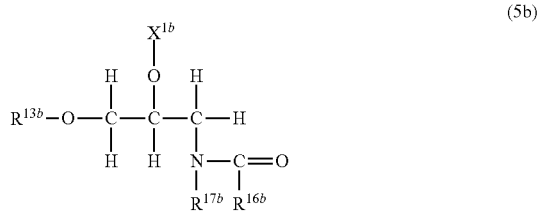

(wherein, $R^{13b}$ represents a linear, branched or cyclic, saturated or unsaturated $C_{10-22}$ hydrocarbon group which may be substituted with a hydroxy group; $X^{1b}$ represents a hydrogen atom, an acetyl group or a glyceryl group; $R^{16b}$ represents a linear, branched or cyclic $C_{5-22}$ hydrocarbon group which may be substituted with a hydroxy or amino group, and which may have, at the ω-end position, an ester-bonded or an amide-bonded $C_{8-22}$ fatty acid moiety that may be linear or branched, saturated or unsaturated, and may be substituted with a hydroxy group; and $R^{17b}$ represents a hydrogen atom or a $C_{1-8}$ alkyl group which may be substituted with a hydroxy, hydroxyalkoxy, alkoxy or acetoxy group).

Preferred examples of $R^{16b}$ include nonyl group, tridecyl group, pentadecyl group, undecyl group having linoleic acid ester-bonded to the ω-position thereof, pentadecyl group having linoleic acid ester-bonded to the ω-position thereof, pentadecyl group having 12-hydroxystearic acid ester-bonded to the ω-position thereof, and undecyl group having methyl-branched isostearic acid amide-bonded to the ω-position thereof. The hydroxyalkoxy or alkoxy group as $R^{17b}$ has preferably 1 to 8 carbon atoms.

As the pseudo type ceramides (5b), those having a hexadecyl group as $R^{13b}$, a hydrogen atom as $X^{1b}$, a pentadecyl group as $R^{16b}$, and a hydroxyethyl group as $R^{17b}$; those having a hexadecyl group as $R^{13b}$, a hydrogen atom as $X^{1b}$, a nonyl group as $R^{16b}$, and a hydroxyethyl group as $R^{17b}$; or those having a hexadecyl group as $R^{13b}$, a glyceryl group as $X^{1b}$, a tridecyl group as $R^{16b}$, and a 3-methoxypropyl group as $R^{17b}$ are preferred, with those of the formula (5b) having a hexadecyl group as $R^{13b}$, a hydrogen atom as $X^{1b}$, a pentadecyl group as $R^{16b}$, and a hydroxyethyl group as $R^{17b}$ being more preferred. Specific preferred examples include compounds having the following structures:

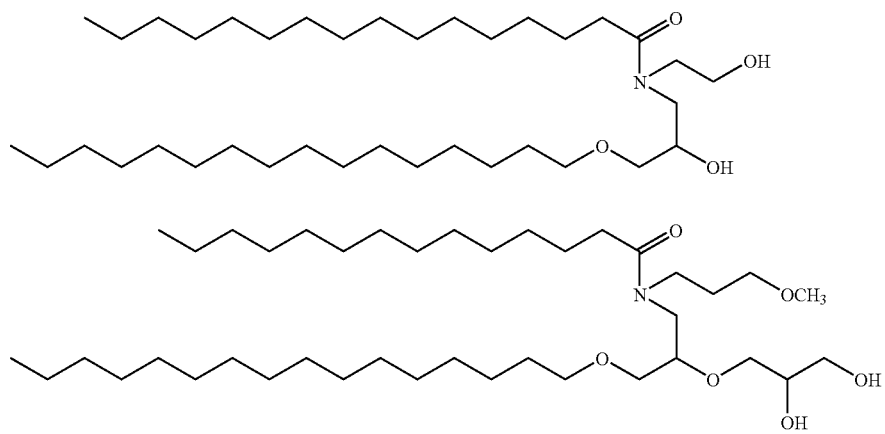

-continued

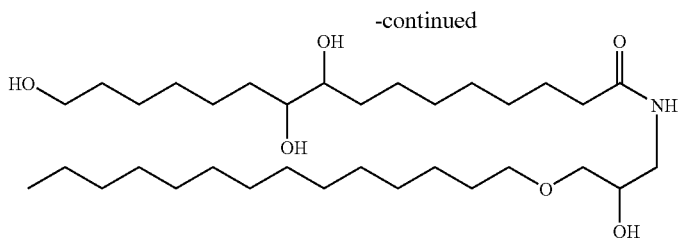

Two or more of these amphipathic amide lipids may be used in combination. The content thereof in the hair cosmetic composition of the present invention is preferably from 0.01 to 10 wt. %, more preferably from 0.05 to 5 wt. % in view of repairing or preventing hair damage.

To the hair cosmetic composition of the present invention, an aromatic alcohol, oil component, cationic surfactant and the like may be added in order to further improve feel to the touch of the hair.

Examples of the aromatic alcohol include benzyl alcohol, cinnamyl alcohol, phenethyl alcohol, p-anisyl alcohol, p-methylbenzyl alcohol, phenoxyethanol, and 2-benzyloxyethanol.

Examples of the oil component include higher fatty acids other than Component (B) such as capric acid, lauric acid, myristic acid, palmitic acid, stearic acid, behenic acid, oleic acid, and coconut oil fatty acid; and hydrocarbon oils such as liquid paraffin, liquid isoparaffin, petrolatum, squalene and squalane. Examples further include natural oils such as camellia oil, Macadamia nut oil, corn oil, olive oil, avocado oil, castor oil, safflower oil, jojoba oil, sunflower oil, rapeseed oil, sesame oil, soybean oil and meadow foam oil; and ester oils such as isopropyl myristate, isopropyl palmitate, myristyl myristate, octyl palmitate, stearyl stearate, isocetyl stearate, isononyl isononanoate, isotridecyl isononanoate, stearic acid hydrogenated castor oil, hydroxystearic acid hydrogenated castor oil, glyceryl tri-2-ethylhexanoate, pentaerythritol tetra-2-ethylhexanoate, neopentyl glycol dicaprate, diglyceryl diisostearate and esters between dipentaerythritol and a mixed fatty acid such as hydroxystearic acid/stearic acid/rosic acid.

Examples of the cationic surfactant include the following compounds (i) to (vi):

(i) Alkyltrimethylammonium salts

Examples of them include compounds represented by the following formula:

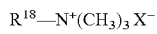

(wherein, $R^{18}$ represents a $C_{12-22}$ alkyl group and $X^-$ represents a halide ion (chloride ion or bromide ion) or an alkyl sulfate ion having 1 or 2 carbon atoms).

(ii) Alkoxytrimethylammonium salts

Examples of them include compounds represented by the following formula:

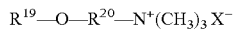

(wherein, $R^{19}$ represents a $C_{12-22}$ alkyl group and $R^{20}$ represents an ethylene or propylene group, and $X^-$ has the same meaning as described above).

(iii) Dialkyldimethylammonium salts

Examples of them include compounds represented by the following formula:

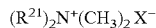

(wherein, $R^{21}$ represents a $C_{12-22}$ alkyl group or a benzyl group and $X^-$ has the same meaning as described above).

(iv) Alkyldimethylamines (and salts thereof)

Examples of them include compounds represented by the following formula:

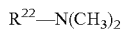

(wherein, $R^{22}$ represents a $C_{12-22}$ alkyl group) and salts thereof.

(v) Hydroxyetheramines (and salts thereof)

Examples of them include compounds represented by the following formula:

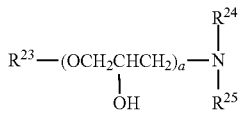

(wherein, $R^{23}$ represents a linear or branched $C_{6-24}$ alkyl or alkenyl group, $R^{24}$ and $R^{25}$ may be the same or different and represents a $C_{1-6}$ alkyl group or a group $-(A^1O)_bH$, in which $A^1$ represents a $C_{2-4}$ alkylene group, b stands for a number from 1 to 6, and b pieces of $A^1$Os may be the same or different and are arranged in any order, and a stands for a number from 1 to 5), and salts thereof.

(vi) Etheramines (and salts thereof)

Examples of them include compounds represented by the following formula:

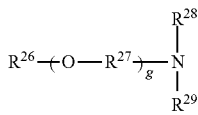

(wherein, $R^{26}$ represents a linear or branched $C_{6-24}$ alkyl or alkenyl group, $R^{27}$ represents a linear or branched $C_{2-5}$ alkylene group, $R^{28}$ and $R^{29}$ individually represent a hydrogen atom, a $C_{1-6}$ alkyl group, or a group $-(A^2O)_hH$, in which $A^2$ represents a $C_{2-4}$ alkylene group, h stands for a number from 1 to 6, and h pieces of $A^2$Os may be the same or different and are arranged in any order, and g stands for an integer from 2 to 8), and salts thereof.

Examples of the cationic surfactants other than those described above in (i) to (vi) include lanolin fatty acid aminopropylethyldimethylammonium ethyl sulfate, lanolin fatty acid aminoethyltriethylammonium ethyl sulfate, lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic acid ($C_{14}$-$C_{20}$)aminopropylethyldimethylammonium ethyl sulfate, isoalkanoic acid ($C_{18}$-$C_{22}$)aminopropylethyldimethylammonium ethyl sulfate, isostearic acid aminopropylethyldimethylammonium ethyl sulfate, isononanoic acid aminopropylethyldimethylammonium ethyl sulfate, and alkyltrimethylammonium saccharin.

As the cationic surfactant, two or more of the above-described ones may be used in combination. The content of the cationic surfactant(s) is preferably from 0.01 to 20 wt. %, more preferably from 0.1 to 15 wt. %, even more preferably from 0.5 to 10 wt. % in order to provide good softness and smoothness to the hair upon use of the hair cosmetic composition.

The hair cosmetic composition of the present invention may further contain components ordinarily employed for hair cosmetic compositions according to the purpose of use. Examples include polymer compounds such as cationic cellulose, hydroxy-alkylated cellulose and highly polymerized polyethylene oxide; nonionic surfactants such as polyoxyethylene alkyl ethers, polyoxyethylene sorbitan fatty acid esters, glycerin fatty acid esters, polyglycerin fatty acid esters, polyoxyethylene hydrogenated castor oils, sucrose fatty acid esters, polyglycerin alkyl ethers, fatty acid alkanolamides, and alkyl glycosides; anti-dandruffs such as zinc pyrithione and benzalkonium chloride; vitamin preparations; bactericides; anti-inflammatory agents; preservatives; chelating agents; humectants such as glycerol and panthenol; colorants such as dyes and pigments; extracts such as extract of Eucalyptus by a polar solvent, protein available from a pearl or a shell having a pearl layer or hydrolysate of the protein, protein available from silk or hydrolysate of the protein, protein-containing extract available from seeds of legume plants, Panax ginseng extract, rice bran extract, fucoid extract, camellia extract, aloe extract, Alpinia Leaf extract and chlorella extract; pearlescent powder such as mica/titanium oxide; fragrances; ultraviolet absorbers; antioxidants; and other components described in *ENCYCLOPEDIA OF SHAMPOO INGREDIENTS* (MICELLE PRESS).

The hair cosmetic composition of the present invention preferably has a pH (at 25° C.) of from 1 to 5.5 when diluted to 20 times the weight with water. When the pH falls within the above-described range, the resulting composition has an improved effect of repairing the hair damage caused by coloring or the like and providing softness and a suppleness to the hair during wetting and even after drying. The pH is adjusted preferably to from 2 to 5, more preferably from 2.5 to 4.5 in view of the repairing effect of damaged hair. For pH adjustment, an acid substance such as inorganic acid or organic acid and a basic substance such as sodium hydroxide can be used in combination. Examples of the inorganic acid and organic acid include the above-described ones used for the neutralization of the amidoamine or etheramine serving as Component (A).

The hair cosmetic composition of the present invention is prepared by dissolving Components (A), (B), and (C) and other optional components in a solvent containing water and, if necessary, ethanol, 2-propanol, glycerin, propylene glycol or the like. It is provided, for example, in the product form of a hair rinse, hair conditioner, leave-on hair treatment or the like.

The following examples further describe and demonstrate embodiments of the present invention. The examples are given solely for the purpose of illustration and are not to be construed as limitations of the present invention.

EXAMPLES

The pH of each of the hair cosmetic compositions which will be described below is measured at 25° C. when the composition is diluted to 20 times its weight with water. Examples 1 to 16 and Comparative Examples 1 to 6

Hair conditioners having the composition as shown in Tables 1 and 2 were prepared and their "softness", "smoothness", "moist feeling", and "suppleness" were evaluated by the following method and criteria. In addition, a fatigue failure resistance test and measurement of contact angle were carried out. It is to be noted that the compositions obtained in Comparative Examples 1 and 4 are the same compositions, but they are compared in Table 1 (a group of amidoamines) and in Table 2 (a group of etheramines), respectively.

Evaluation Method:

A tress of 20 g (from about 15 to 20 cm in length) of Japanese female hair subjected to cosmetic treatment such as cold waving, bleaching or the like was shampooed. To the resulting hair tress was applied uniformly 2 g of each of the hair conditioners, followed by rinsing with running water for 30 seconds. After towel drying and blow drying, "softness", "smoothness", "moist feeling" and "suppleness" of the hair tress was organoleptically evaluated by five panelists. The total of their scores is shown in the Tables.

Evaluation Criteria:
"Softness"
   4:Very soft
   3:Soft
   2:Not so soft
   1:Not soft
"Smoothness"
   4:Very smooth
   3:Smooth
   2:Not so smooth
   1:Not smooth
"Moist feeling"
   4:very moisturized
   3:Moisturized
   2:Not so moisturized
   1:Not moisturized
"Suppleness"
   4:very supple
   3:Supple
   2:Not so supple
   1:Not supple
"Fatigue Failure Resistance Test"

In accordance with the method as described in Y. K. Kamath, S. B. Hornby, H. D. Weigmann, and S. Ruetsch, J. Cos. Sci., 50, 198-200(1999), a load of 50 g/hair was applied in repetition and the number of repetitions until the hair was broken was counted. Based on the resulting data, a parameter of fatigue failure resistance (characteristic life) was calculated as described below.

To statistically analyze the fatigue failure behavior, "Weibull distribution" by which characteristic in variation can be evaluated over a wide range is employed. In the equation (a) of Weibull distribution, a parameter θ (characteristic life) is determined from the equation (b) available by taking natural logarithm on both sides twice. An approximate curve is determined by plotting each data with an x-axis as ln x and a y axis as ln ln {1/[1−F(x)]} and the parameter θ is calculated from an intercept=b ln θ; and gradient=b (equation (c)).

$$F(x)=1-\exp[-(x/\theta)^b] \quad (a)$$

$$\ln\ln\{1/[1-F(x)]\}=b\ln x - b\ln\theta \quad (b)$$

$$\theta \text{ (Characteristic life)}=\exp(-\text{intercept}/\text{gradient}) \quad (c)$$

x: the number of repetitions at which the hair is broken
F(x): breakage order/the population
b: shape parameter
θ: characteristic life (number of repetitions at which 63.2% of the populations is broken)
"Measurement of Contact Angle"

The contact angle of the hair (N=10) shampooed once after treatment with each of the hair cosmetic compositions was measured in accordance with the method as described in Watanabe, JSCCJ, 29(1), 64-68(1995).

TABLE 1

|   | (wt. %) | Example 1 | Example 2 | Example 3 | Example 4 | Example 5 | Example 6 | Example 7 | Example 8 | Comp. Ex. 1 | Comp. Ex. 2 | Comp. Ex. 3 |
|---|---|---|---|---|---|---|---|---|---|---|---|---|
| (A) | Stearic acid dimethylaminopropylamide | 1.0 | 1.0 | 1.0 | 1.0 | 1.0 | 1.0 | 1.0 | 1.0 | — | 1.0 | 1.0 |
| (A)' | Stearyltrimethylammonium chloride | — | — | — | — | — | — | — | — | 1.0 | — | — |
| (B) | 18-Methyleicosanoic acid | 0.5 | 0.5 | 0.5 | 0.5 | 0.5 | — | — | — | 0.5 | 0.5 | — |
|  | 16-Methylheptadecanoic acid | — | — | — | — | — | 0.5 | — | — | — | — | — |
|  | 17-Methyloctadecanoic acid | — | — | — | — | — | — | 0.5 | — | — | — | — |
|  | Lanolin fatty acid salt[*1] | — | — | — | — | — | — | — | 0.5 | — | — | — |
| (B)' | Oleic acid | — | — | — | — | — | — | — | — | — | — | 1.0 |
| (C) | Dimethicone[*2] | 2.0 | 2.0 | 2.0 | 2.0 | — | 2.0 | 2.0 | 2.0 | 2.0 | — | 2.0 |
|  | Amino-modified silicone[*3] | — | — | — | 0.5 | 0.5 | — | — | — | — | — | — |
| (D) | Amphiphatic amide lipid A[*4] | — | 0.5 | — | — | — | — | — | — | — | — | — |
|  | Amphiphatic amide lipid B[*5] | 0.5 | — | — | — | — | — | — | — | — | — | — |
| Others | Stearyl alcohol | 3.0 | 3.0 | 3.0 | 3.0 | 3.0 | 3.0 | 3.0 | 3.0 | 3.0 | 3.0 | 3.0 |
|  | pH regulator (sodium hydroxide, lactic acid) | q.s. | q.s. | q.s. | q.s. | q.s. | q.s. | q.s. | q.s. | q.s. | q.s. | q.s. |
|  | Deionized water | Balance | Balance | Balance | Balance | Balance | Balance | Balance | Balance | Balance | Balance | Balance |
|  | pH | 3.2 | 3.2 | 3.2 | 3.2 | 3.2 | 3.2 | 3.2 | 3.2 | 3.2 | 3.2 | 3.2 |
| Evaluation | Softness | 20 | 19 | 16 | 20 | 18 | 20 | 20 | 19 | 9 | 7 | 9 |
|  | Smoothness | 19 | 17 | 16 | 18 | 17 | 19 | 18 | 19 | 10 | 5 | 9 |
|  | Moist feeling | 20 | 19 | 19 | 20 | 17 | 17 | 18 | 19 | 11 | 6 | 10 |
|  | Suppleness | 18 | 19 | 15 | 20 | 18 | 19 | 19 | 19 | 13 | 8 | 9 |
|  | Characteristic life 0 (times) | 61000 | 67000 | 70000 | 65000 | 68000 | 66000 | 65000 | 61000 | 41000 | 44000 | 37000 |
|  | Contact angle after shampooing (°) | 95 | 94 | 91 | 97 | 96 | 92 | 96 | 91 | 64 | 62 | 60 |

[*1] 18-MEA (trade name; product of Croda Japan)
[*2] "SH200C" (trade name; product of Dow Corning Toray, viscosity: 100000 mm$^2$/s)
[*3] "SM8704C" (trade name; product of Dow Corning Toray)
[*4] Amphiphatic amide lipid A:

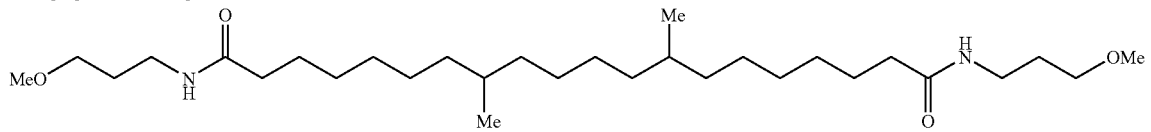

[*5] Amphiphatic amide lipid B

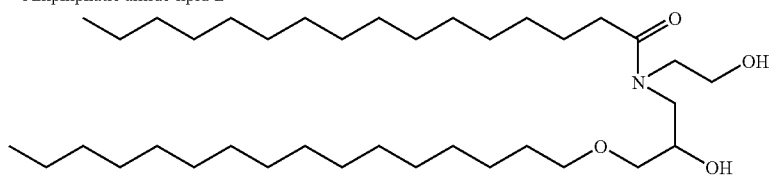

TABLE 2

|   | (wt. %) | Example 9 | Example 10 | Example 11 | Example 12 | Example 13 | Example 14 | Example 15 | Example 16 | Comp. Ex. 4 | Comp. Ex. 5 | Comp. Ex. 6 |
|---|---|---|---|---|---|---|---|---|---|---|---|---|
| (A) | N,N-Dimethyl-3-octadecyloxypropylamine | 1.0 | 1.0 | 1.0 | 1.0 | 1.0 | 1.0 | 1.0 | 1.0 | — | 1.0 | 1.0 |
| (A)' | Stearyltrimethylammonium chloride | — | — | — | — | — | — | — | — | 1.0 | — | — |
| (B) | 18-Methyleicosanoic acid | 0.5 | 0.5 | 0.5 | 0.5 | 0.5 | — | — | — | 0.5 | 0.5 | — |
|  | 16-Methylheptadecanoic acid | — | — | — | — | — | 0.5 | — | — | — | — | — |
|  | 17-Methyloctadecanoic acid | — | — | — | — | — | — | 0.5 | — | — | — | — |
|  | Lanolin fatty acid salt[*1] | — | — | — | — | — | — | — | 0.5 | — | — | — |
| (B)' | Oleic acid | — | — | — | — | — | — | — | — | — | — | 1.0 |
| (C) | Dimethicone[*2] | 2.0 | 2.0 | 2.0 | 2.0 | — | 2.0 | 2.0 | 2.0 | 2.0 | — | 2.0 |
|  | Amino-modified silicone[*3] | — | — | — | 0.5 | 0.5 | — | — | — | — | — | — |
| (D) | Amphiphatic amide lipid A[*4] | — | 0.5 | — | — | — | — | — | — | — | — | — |
|  | Amphiphatic amide lipid B[*5] | 0.5 | — | — | — | — | — | — | — | — | — | — |
| Others | Stearyl alcohol | 3.0 | 3.0 | 3.0 | 3.0 | 3.0 | 3.0 | 3.0 | 3.0 | 3.0 | 3.0 | 3.0 |
|  | pH regulator (sodium hydroxide, lactic acid) | q.s. | q.s. | q.s. | q.s. | q.s. | q.s. | q.s. | q.s. | q.s. | q.s. | q.s. |

TABLE 2-continued

|  | (wt. %) | Examples | | | | | | | | Comparative Examples | | |
|---|---|---|---|---|---|---|---|---|---|---|---|---|
|  |  | 9 | 10 | 11 | 12 | 13 | 14 | 15 | 16 | 4 | 5 | 6 |
|  | Deionized water | Balance | Balance | Balance | Balance | Balance | Balance | Balance | Balance | Balance | Balance | Balance |
|  | pH | 3.2 | 3.2 | 3.2 | 3.2 | 3.2 | 3.2 | 3.2 | 3.2 | 3.2 | 3.2 | 3.2 |
| Evaluation | Softness | 20 | 19 | 15 | 19 | 20 | 20 | 19 | 20 | 10 | 8 | 10 |
|  | Smoothness | 20 | 20 | 17 | 18 | 17 | 20 | 17 | 18 | 11 | 5 | 8 |
|  | Moist feeling | 19 | 19 | 17 | 18 | 19 | 18 | 20 | 20 | 12 | 5 | 11 |
|  | Suppleness | 20 | 20 | 15 | 19 | 19 | 20 | 19 | 19 | 10 | 9 | 8 |
|  | Characteristic life 0 (times) | 62000 | 65000 | 69000 | 66000 | 67000 | 64000 | 65000 | 60000 | 38000 | 48000 | 32000 |
|  | Contact angle after shampooing (°) | 96 | 93 | 92 | 95 | 95 | 92 | 95 | 90 | 65 | 61 | 62 |

*[1] 18-MEA (trade name; product of Croda Japan)
*[2] "SH200C" (trade name; product of Dow Corning Toray, viscosity: 100000 mm$^2$/s)
*[3] "SM8704C" (trade name; product of Dow Corning Toray)
*[4] Amphiphatic amide lipid A:

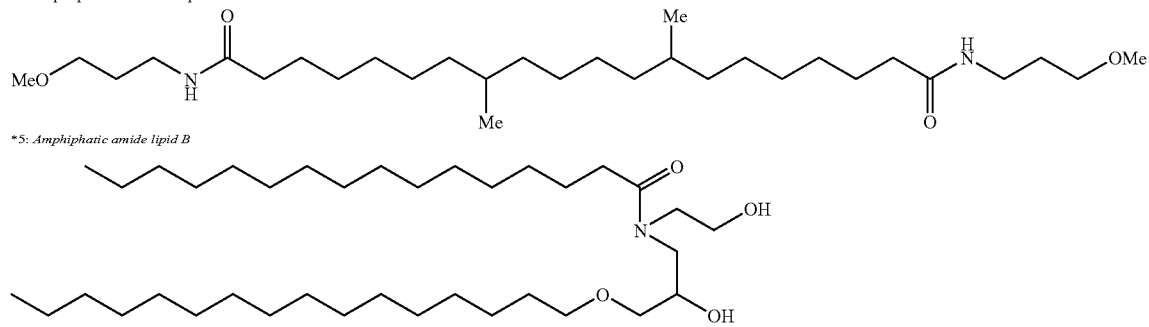

*[5]: Amphiphatic amide lipid B

Example 17

Hair Conditioner (pH 4.5)

| | (wt. %) |
|---|---|
| Stearic acid dimethylaminopropylamide | 0.5 |
| Stearyl alcohol | 3.0 |
| Benzyloxyethanol | 0.3 |
| Stearyltrimethylammonium chloride | 1.0 |
| Myristic acid | 0.2 |
| Isotridecyl myristate | 0.5 |
| Aminoethylaminopropylsiloxane/dimethylsiloxane copolymer emulsion | 0.5 |
| Dimethylpolysiloxane | 3.0 |
| Propylene glycol | 1.0 |
| Malic acid | 0.1 |
| 18-Methyleicosanoic acid | 0.5 |
| Amphiphatic amide lipid B | 0.1 |
| Fragrance | 0.4 |
| Methylparaben | 0.3 |
| Sodium hydroxide | q.s. |
| Deionized water | Balance |

The hair conditioner having the above-described composition can repair or prevent damage and/or fatigue failure of the hair and provide the hair with good softness and suppleness during wetting and even after drying.

Example 18

Hair Treatment (pH 4.0)

| | (wt. %) |
|---|---|
| Behenic acid dimethylamionopropylamide | 2.0 |
| Behenyltrimethylammonium chloride | 0.3 |
| Stearyl alcohol | 4.5 |
| Behenyl alcohol | 1.5 |
| Isononyl isononanoate | 0.5 |
| Methylpolysiloxane mixture | 2.5 |
| Aminoethylaminopropylsiloxane/dimethylsiloxane copolymer emulsion | 0.5 |
| Glycolic acid | 0.5 |
| Malic acid | 0.1 |
| Dipropylene glycol | 3.0 |
| Benzyl alcohol | 0.3 |
| Amphiphatic amide lipid B | 0.1 |
| Arginine | 0.2 |
| 16-Methyloctadecanoic acid | 0.5 |
| Pantothenyl ethyl ether | 0.1 |
| Fragrance | 0.4 |
| Methylparaben | 0.1 |
| Sodium hydroxide | q.s. |
| Deionized water | Balance |

The hair treatment having the above-described composition can repair or prevent damage and/or fatigue failure of the hair and provide the hair with good softness and suppleness during wetting and even after drying.

Example 19

Hair Conditioner (pH 3.3)

|  | (wt. %) |
|---|---|
| N,N-Dimethyl-3-octadecyloxypropylamine | 2.0 |
| Stearyl alcohol | 5.0 |
| Dipropylene glycol | 1.0 |
| Benzyl alcohol | 0.5 |
| Phenoxyethanol | 0.1 |
| Glycerin | 5.0 |
| Polypropylene glycol | 2.5 |
| 18-Methyleicosanoic acid | 0.5 |
| Amphiphatic amide lipid B | 0.1 |
| Sunflower oil | 0.5 |
| Methylpolysiloxane mixture | 2.5 |
| Lactic acid | 1.5 |
| Fragrance | 0.4 |
| Sodium hydroxide | q.s. |
| Deionized water | Balance |

The hair conditioner having the above-described composition can repair or prevent damage and/or fatigue failure of the hair and provide the hair with softness and suppleness during wetting and even after drying.

Example 20

Hair Conditioner (pH 3.3)

|  | (wt. %) |
|---|---|
| N,N-Dimethyl-3-octadecyloxypropylamine | 2.0 |
| Stearic acid dimethylaminopropylamide | 2.0 |
| Stearyl alcohol | 5.0 |
| Dipropylene glycol | 1.0 |
| Benzyl alcohol | 0.5 |
| Phenoxyethanol | 0.1 |
| Glycerin | 5.0 |
| Polypropylene glycol | 2.5 |
| 18-Methyleicosanoic acid | 0.5 |
| Amphiphatic amide lipid B | 0.1 |
| Sunflower oil | 0.5 |
| Methylpolysiloxane mixture | 2.5 |
| Lactic acid | 1.5 |
| Fragrance | 0.4 |
| Sodium hydroxide | q.s. |
| Deionized water | Balance |

The hair conditioner having the above-described composition can repair or prevent damage and/or fatigue failure of the hair and provide the hair with good softness and suppleness during wetting and even after drying.

Example 21

Hair Conditioner (pH 3.3)

|  | (wt. %) |
|---|---|
| Hexadecyloxy(2-hydroxypropyl)dimethylamine | 0.5 |
| N,N,N-Trimethylammonium chloride | 2.0 |
| Stearyl alcohol | 5.0 |
| Dipropylene glycol | 1.0 |
| Benzyl alcohol | 0.5 |
| Phenoxyethanol | 0.1 |
| Glycerin | 5.0 |
| Polypropylene glycol | 2.5 |
| 18-Methyleicosanoic acid | 0.5 |
| Amphiphatic amide lipid B | 0.1 |
| Sunflower oil | 0.5 |
| Methylpolysiloxane mixture | 2.5 |
| Lactic acid | 1.5 |
| Fragrance | 0.4 |
| Sodium hydroxide | q.s. |
| Deionized water | Balance |

The hair conditioner having the above-described composition can repair or prevent damage and/or fatigue failure of the hair and provide the hair with good softness and suppleness during wetting and even after drying.

Example 22

Hair Treatment (pH 3.3)

|  | (wt. %) |
|---|---|
| N,N-Dimethyl-3-octadecyloxypropylamine | 2.0 |
| Stearyl alcohol | 9.0 |
| Glutamic acid | 1.5 |
| Benzyloxyethanol | 1.0 |
| Dipropylene glycol | 2.0 |
| Phenoxyethanol | 0.1 |
| Amphiphatic amide lipid B | 0.1 |
| Dipentaerythritol fatty acid ester | 0.2 |
| 16-Methyloctadecanoic acid | 0.5 |
| Methylpolysiloxane mixture | 2.5 |
| Highly-polymerized methylpolysiloxane/decamethylcyclopentasiloxane mixture | 2.5 |
| Aminoethylaminopropylsiloxane/dimethylsiloxane copolymer emulsion | 0.5 |
| Hydroxyethyl cellulose | 0.3 |
| Paraffin | 0.5 |
| Fragrance | 0.3 |
| Sodium hydroxide | q.s. |
| Deionized water | Balance |

The hair treatment having the above-described composition can repair or prevent damage and/or fatigue failure of the hair and provide the hair with good softness and suppleness during wetting and even after drying.

The invention claimed is:
1. A hair cosmetic composition comprising the following Components (A), (B), (C) and water:
(A): 0.1 to 20 wt. % of an etheramine represented by the following formula (2) or a salt thereof:

(2)

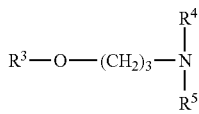

wherein, $R^3$ represents a linear or branched $C_{6-24}$ alkyl or alkenyl group, $R^4$ and $R^5$ may be the same or different and each represents a $C_{1-6}$ alkyl group;

(B) 0.01 to 10 wt. % of one or more branched fatty acid selected from the group consisting of 18-methyl-eicosanoic acid, 14-methylpentadecanoic acid, 14-methylhexadecanoic acid, 15-methylhexadecanoic acid, 15-methyl heptadecanoic acid, 16-methylheptadecanoic acid, 16-methyloctadecanoic acid, 17-methyloctadecanoic acid, 17-methylnonadecanoic acid and lanolin fatty acid; and (C) 0.1 to 15 wt. % of a silicon;

wherein wt. % is based on the total weight of the hair cosmetic composition.

2. The hair cosmetic composition according to claim 1, further comprising an amphiphatic amide lipid as Component (D).

3. The hair cosmetic composition according to claim 2, wherein Component (D) is a diamide compound represented by the following formula (4):

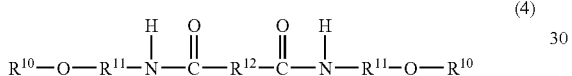

(4)

wherein, $R^{10}$ represents a linear or branched $C_{1-12}$ hydrocarbon group which may be substituted with a hydroxy group and/or an alkoxy group, $R^{11}$ represents a linear or branched divalent $C_{1-5}$ hydrocarbon group, and $R^{12}$ represents a linear or branched divalent $C_{1-22}$ hydrocarbon group.

4. The hair cosmetic composition according to claim 2, wherein Component (D) is a ceramide represented by the following formula (5):

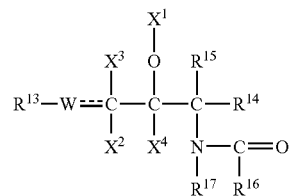

(5)

wherein, $R^{13}$ represents a linear, branched or cyclic, and saturated or unsaturated $C_{4-30}$ hydrocarbon group which may be substituted with a hydroxy, oxo or amino group; W represents a methylene group, a methine group or an oxygen atom, a broken line represents the presence or absence of a πbond; $X^1$ represents a hydrogen atom, an acetyl group or a glyceryl group, or forms an oxo group together with the adjacent oxygen atom; $X^2$, $X^3$ and $X^4$ each independently represent a hydrogen atom, a hydroxy group or an acetoxy group, with the proviso that when W represents a methine group, either $X^2$ or $X^3$ represents a hydrogen atom and the other does not exist, and when —O —$X^1$ represents an oxo group, $X^4$ does not exist; $R^{14}$ and $R^{15}$ each independently represents a hydrogen atom, a hydroxy group, a hydroxymethyl group, or an acetoxymethyl group; $R^{16}$ represents a linear, branched or cyclic $C_{5-35}$ hydrocarbon group which may be substituted with a hydroxy or amino group, and which may have, at the ω-position, an ester-bonded or an amide-bonded $C_{8-22}$ fatty acid moiety that may be linear, branched or cyclic, and saturated or unsaturated, and may be substituted with a hydroxy group; and $R^{17}$ represents a hydrogen atom or a linear or branched, and saturated or unsaturated $C_{1-8}$ hydrocarbon group which may be substituted with a hydroxy group, hydroxyalkoxy groups, alkoxy groups and an acetoxy group.

5. The hair cosmetic composition according to claim 1, having a pH value at 25° C. of from 1 to 5.5 when diluted to 20 times the weight with water.

* * * * *